(12) United States Patent
Kogiso

(10) Patent No.: US 10,068,498 B2
(45) Date of Patent: Sep. 4, 2018

(54) ORGAN MODEL FOR ENDOSCOPE

(71) Applicant: OLYMPUS CORPORATION, Hachioji-shi, Tokyo (JP)

(72) Inventor: Junichi Kogiso, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/348,274

(22) Filed: Nov. 10, 2016

(65) Prior Publication Data
US 2017/0061830 A1 Mar. 2, 2017

Related U.S. Application Data

(63) Continuation of application No. PCT/JP2015/065548, filed on May 29, 2015.

(30) Foreign Application Priority Data

Jun. 5, 2014 (JP) .................. 2014-116808

(51) Int. Cl.
G09B 23/30 (2006.01)
A61B 1/00 (2006.01)

(52) U.S. Cl.
CPC .......... G09B 23/30 (2013.01); A61B 1/00057 (2013.01); G09B 23/306 (2013.01); A61B 1/00 (2013.01)

(58) Field of Classification Search
None
See application file for complete search history.

(56) References Cited

FOREIGN PATENT DOCUMENTS

| JP | 2004-049479 A | 2/2004 |
| JP | 2006-116206 A | 5/2006 |
| JP | 2008-197483 A | 8/2008 |
| JP | 2014-095870 A | 5/2014 |
| WO | 2013/069143 A1 | 5/2013 |

OTHER PUBLICATIONS

Aug. 25, 2015 Search Report issued in International Patent Application No. PCT/JP2015/065548.
Mar. 8, 2016 Office Action issued in Japanese Patent Application No. 2015-560430.
Sep. 13, 2016 Office Action issued in Japanese Patent Application No. 2015-560430.

Primary Examiner — James Hull
(74) Attorney, Agent, or Firm — Oliff PLC

(57) ABSTRACT

An organ model for endoscope includes: a basic shape part formed by imitating a shape of a tubular organ; and a tissue holding part that holds a tissue piece and is detachably provided with respect to the basic shape part. The tissue holding part includes: a main body that is formed in a tubular shape and has a window part communicating with an internal space, on an outer peripheral surface; and a fixing member that fixes the tissue piece on the main body such that at least a portion of the tissue piece overlaps the window part. The main body is rotatable in a circumferential direction of the main body with respect to the basic shape part, in a state where the main body is attached to the basic shape part.

3 Claims, 4 Drawing Sheets

ORGAN MODEL FOR ENDOSCOPE

CROSS REFERENCE TO RELATED APPLICATIONS

This application is a continuation application based on a PCT Patent Application No. PCT/JP2015/065548, filed on May 29, 2015, whose priority is claimed on Japanese Patent Application No. 2014-116808, filed on Jun. 5, 2014, the entire content of which are hereby incorporated by reference.

BACKGROUND OF THE INVENTION

Field of the Invention

The present invention relates to an organ model for endoscope, and more specifically, to an organ model for endoscope used for training for the operation of a flexible endoscope or the like, performance evaluation of the flexible endoscope or the like, or the like.

Description of the Related Art

In the related art, in training for the operation of a flexible endoscope or the like, performance evaluation of the flexible endoscope or the like, organ models for endoscope formed by imitating internal organs of humans are used.

Such organ models for endoscope are also used for training for various endoscope operations. However, in training of procedures, such as endoscopic mucous membrane dissection or suturing, it is necessary to use actual internal organ tissue. Therefore, it is more general to configure at least a portion where a procedure is performed, using sections of internal organ tissues of pigs, cows, or the like.

An incision dissection model for endoscope, including an imitation internal organ having the shape of a predetermined internal organ, and a fixing frame that can fix mucous membrane tissue, is described in Japanese Unexamined Patent Application, First Publication No. 2006-116206. The fixing frame is incorporated into a window provided in the imitation internal organ.

SUMMARY

According to a first aspect of the invention, there is provided an organ model for endoscope including a basic shape part formed by imitating the shape of a tubular organ; and a tissue holding part that holds a tissue piece and is detachably provided with respect to the basic shape part. The tissue holding part includes a main body that is formed in a tubular shape and has a window part communicating with an internal space, on an outer peripheral surface, and a fixing member that fixes the tissue piece on the main body such that at least a portion of the tissue piece overlaps the window part. The main body is rotatable in a circumferential direction of the main body with respect to the basic shape part, in a state where the main body is attached to the basic shape part.

According to a second aspect of the invention, in the organ model for endoscope of the first aspect, the fixing member may have a projection part, and the main body may have a fixing hole that communicates with the internal space and allows projection part to enter thereinto.

According to a third aspect of the invention, in the organ model for endoscope of the second aspect, the fixing hole may be provided at a position that does not overlap the window part in an axial direction of the main body.

DETAILED DESCRIPTION OF THE PREFERRED EMBODIMENTS

An embodiment of the invention will be described with reference to FIGS. 1 to 7.

Figure 1:
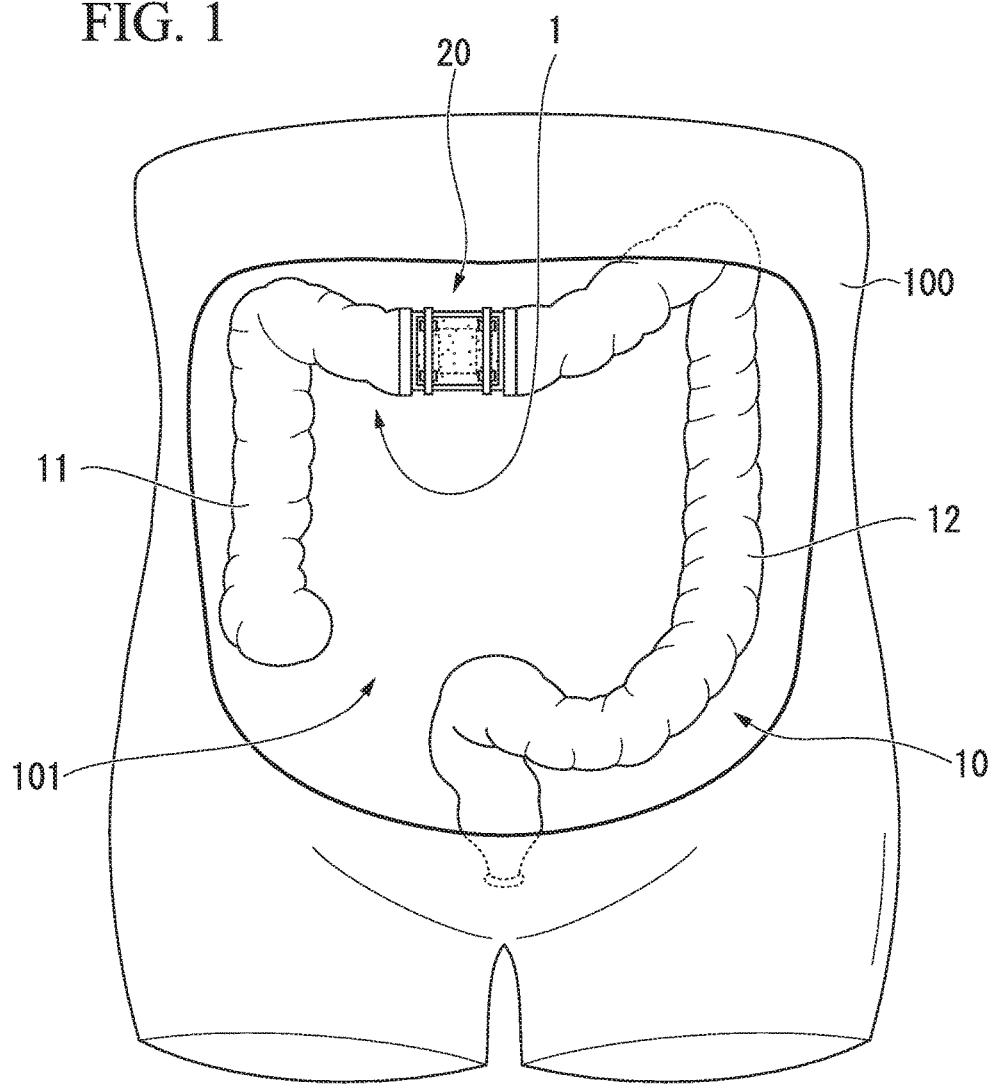
FIG. 1 is a view illustrating an organ model for endoscope related to an embodiment of the invention.

FIG. 1 is a view illustrating a housing 100 with that an organ model 1 for endoscope of the present embodiment is housed. The housing 100 is formed in a shape that imitates the body of a human, using resin or the like, and has an internal space 101 capable of housing the organ model 1 for endoscope. The organ model 1 for endoscope is a model that imitates the large intestine (tubular organ) of a human, and includes a tubular flexible part (basic shape part) 10 formed by imitating the large intestine, and a tissue holding part 20 that is rotatably attached to and detached from the flexible part 10.

The flexible part 10 is formed using, for example, flexible materials, such as silicone, and defines a basic shape of the organ model 1 for endoscope. The flexible part 10 has a first flexible part 11 that imitates the large intestine on a proximal side, and a second flexible part 12 that imitates the large intestine on the distal side. One end of the second flexible part 12 is connected to a hole (not illustrated) provided in the housing 100. Since the hole to which the second flexible part 12 is connected is provided at a position of the housing 100 equivalent to the anus, training or evaluation regarding an insertion procedure of an endoscope can be performed by disposing the flexible part 10 in the internal space 101 of the housing 100, similar to a traveling aspect of the large intestine of a human.

Figure 2:
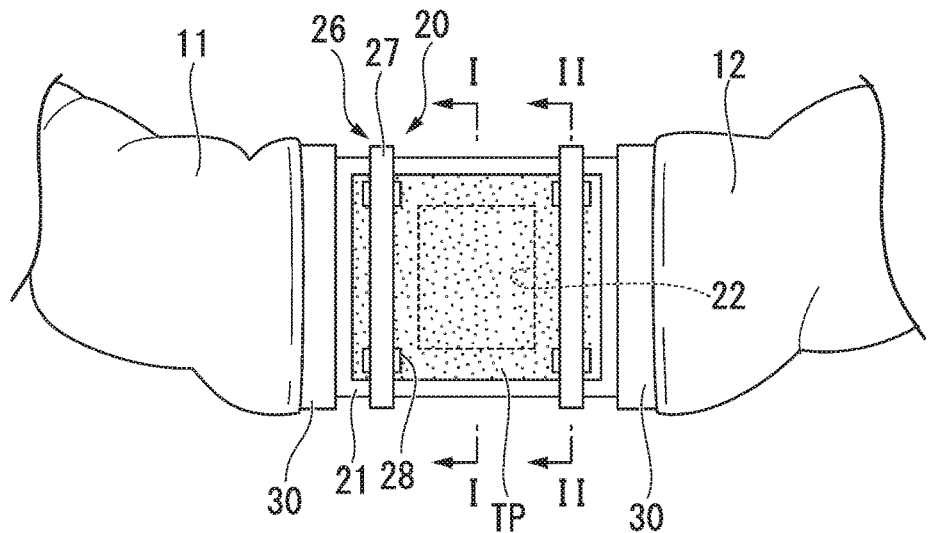
FIG. 2 is an enlarged view illustrating a tissue holding part and its periphery of the organ model for endoscope.
Figure 3:
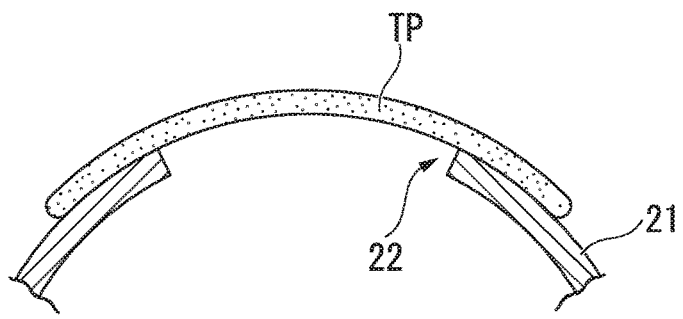
FIG. 3 is a sectional view taken along line I-I of FIG. 2.
Figure 4:
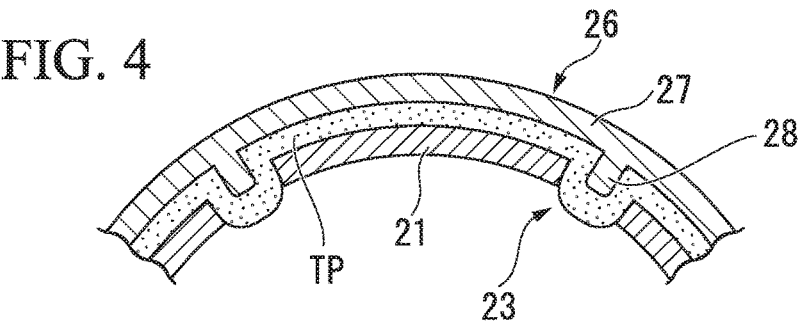
FIG. 4 is a sectional view taken along line II-II of FIG. 2.

FIG. 2 is an enlarged view illustrating the tissue holding part 20 and its periphery. FIG. 3 is a sectional view taken along line I-I of FIG. 2, and FIG. 4 is a sectional view taken along line II-II of FIG. 2.

Figure 5:
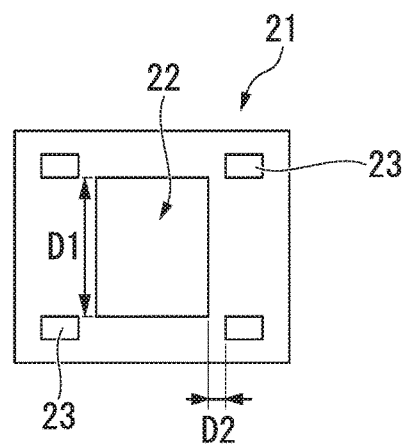
FIG. 5 is a view illustrating a main body of the tissue holding part.

The tissue holding part 20 includes a substantially cylindrical main body 21, and fixing members 26 attached to the main body 21. FIG. 5 is a plan view of the main body 21. An window part 22 for exposing tissue the inside of the organ model 1 for endoscope and four fixing holes 23 provided around the window part 22 are provided in the main body 21 so as to communicate with the internal space through a peripheral wall of the main body 21.

The dimensions of the window part 22 may be appropriately set in consideration of what size of tissue is desired to expose to the inside of the organ model 1 for endoscope. Additionally, the shape of the window part is also not limited to a quadrangular shape, and may be set appropriately. However, it is preferable that a dimension D1 of the window part in a circumferential direction of the main body 21 is approximately equal to or smaller than ¼ of the outer peripheral length of the main body 21. If the dimension of the window part in the circumferential direction of the main body is too large, a support state of tissue to be exposed to the window part may become unnatural. As a result, there may be deviation from actual internal organs, which is not preferable.

In the present embodiment, the fixing holes 23 are provided at positions that do not overlap the window part 22 in any of the axial direction and the circumferential direction of the main body 21. Although the number of the fixing holes 23 or positions where the fixing holes 23 are provided are set appropriately, it is preferable if the fixing holes are provided at least at the positions that do not overlap the window part 22 in the axial direction of the main body 21 because the fixing members 26 are easily disposed so as not to overlap the window part 22.

A fixation margin D2 that is a distance between the fixing holes 23 and the window part 22 is equal to or greater than, for example, 3 mm, tissue can be suitably held by the main body. If the shape of the fixing holes is set to be longer in the circumferential direction than in the axial direction of the main body 21, it becomes easy to absorb errors in a fixing operation to be described below, which is preferable.

The fixing members 26 have a stringy or beltlike band part 27, and projection parts 28 provided on the band part 27. The band part 27 can be formed of resin, cloth, or the like, and can be formed in an annular shape, thereby clamping a tissue piece disposed on an outer peripheral surface of the main body 21. The projection parts 28 have a shape capable of entering the fixing holes 23.

As illustrated in FIG. 2, tubular connecting members 30 are attached to end parts of the first flexible part 11 and the second flexible part 12. There is no particular limitation to connection aspects between the connecting members 30 and the flexible part 10. For example, the end parts of the flexible part 10 may be expanded and fitted into the connecting members, or the connecting members may be bonded connected to the flexible part 10.

The internal diameter of the connecting members 30 is slightly greater than the external diameter of the main body 21. If end parts of the main body 21 are made to enter the connecting members 30, light friction occurs between inner surfaces of the connecting members 30 and an outer surface of the main body 21, and the flexible part 10 and the tissue holding part 20 are engaged with each other. The tissue holding part 20 can be rotated around a shaft of the main body 21 with respect to the engaged flexible part 10 by applying a predetermined force.

The operation when the organ model 1 for endoscope of the present embodiment configured described above is used will be described.

First, a tissue piece to be attached to the tissue holding part 20 is prepared. A tissue piece of a size such that the window part 22 and all the fixing holes 23 are covered is cut out from an internal organ or the like of an animal that is appropriately selected in consideration of procedures, sites, or the like.

Next, a surface of a tissue piece that is desired to be exposed to the inside of the organ model, and the outer peripheral surface or the like of the main body 21 are made to face each other, and a tissue piece TP is disposed on the outer peripheral surface of the main body 21 so as to overlap the window part 22 and the fixing holes 23. Subsequently, the two fixing members 26 are annularly attached with the projection parts 28 being made to face the tissue piece TP, and the tissue piece TP is clamped to the main body 21. In this case, the positions of the projection parts 28 and the positions of the fixing holes 23 are aligned with each other, and the fixing members 26 are attached such that the projection parts 28 enter the fixing holes 23. The fixation of the tissue piece TP to the tissue holding part 20 is completed above.

In a state where the tissue piece TP is fixed to the tissue holding part 20, as illustrated in FIG. 4, portions of the tissue piece TP are pushed by the projection parts 28 of the fixing members 26, and enter the fixing holes 23. Accordingly, the tissue piece TP is suitably prevented from deviating in the circumferential direction and in the longitudinal direction of the main body 21 with respect to the main body 21. Additionally, portions of the tissue piece TP, as illustrated in FIG. 3, are exposed the inside of the organ model 1 for endoscope from the window part 22, in a state where a tension is moderately applied, and is supported in a state where a procedure is performed by the endoscope inserted into the flexible part 10.

After the tissue piece TP is fixed to the tissue holding part 20, both of the end parts of the main body 21 are made to enter the connecting members 30 that are respectively attached to the first flexible part 11 and the second flexible part. Accordingly, the tissue holding part 20 and the flexible part 10 are engaged with each other, and the first flexible part 11 and the second flexible part 12 are integrally connected via the tissue holding part 20. If the tissue holding part 20 is rotated in the circumferential direction of the main body 21 with respect to the flexible part 10 and the window part 22 is moved to a desired position if necessary, the organ model 1 for endoscope is brought into an available state.

A user can perform various kinds of training or performance evaluation (hereinafter referred to as "training or the like") of the endoscope, the treatment tool, or the like by inserting the endoscope into the flexible part 10 or performing a procedure on the tissue exposed from the window part 22 using the treatment tool inserted into the endoscope. In a case where training regarding a procedure or the like is performed, the training or the like can be continuously performed by preparing a plurality of the tissue holding parts 20 to which tissue pieces are fixed in advance, and by sequentially replacing the tissue holding parts with each other. In a case where training is performed using a treatment tool, such as a high-frequency knife, to be energized, energization to the tissue piece TP may be allowed by attaching opposite pole members having conductivity to the end parts of the tissue piece TP or connecting opposite pole members attached to separated positions and the tissue piece TP, with a gauze made to become wet with a physiological salt solution.

Since nothing that supports the tissue piece TP exists on a side opposite to the side of the tissue piece TP exposed to the window part 22, the state of a tension or the like to act on the tissue exposed to the window part 22, is very similar to that of an actual internal organ. Therefore, for example, when training of ESD (endoscopic submucosal dissection) or the like is performed on the tissue piece TP, behavior, sensation, or the like of tissue when such an operation that a tip part of the endoscope is made to be hidden under a mucous membrane is performed is also obtained similar to a case where such as operation is performed on an actual patient.

As described above, according to the organ model 1 for endoscope of the present embodiment, the tissue holding part 20 by which the tissue piece TP is held is rotatably attached around the axis with respect to the flexible part 10, the window part 22 to which tissue is exposed can be moved at a desired position without rotating the flexible part 10. As a result, various situations, such as a case where tissue to be subjected to a procedure is on a belly side or a case where tissue is on a back side, can be reproduced easily, and training or the like can be performed with diversity being guaranteed with an easy operation.

When training or the like is performed using the organ model 1 for endoscope, tissue may be not necessarily fixed to the tissue holding part. For example, paper or the like is fixed to the tissue holding part, and a recording jig that can leave the track of a tip on the paper or the like instead of a treatment tool, such as a high-frequency knife, is inserted into a channel of the endoscope. By operating the recording jig protruded from the tip of the endoscope in this state, the track of the tip of the recording jig can be recorded on the paper, and the training or the like can be performed.

Figure 6:
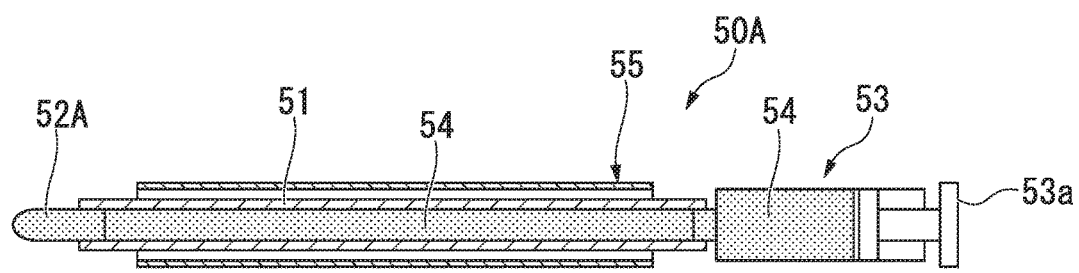
FIG. 6 is a view illustrating an example of a recording jig.
Figure 7:
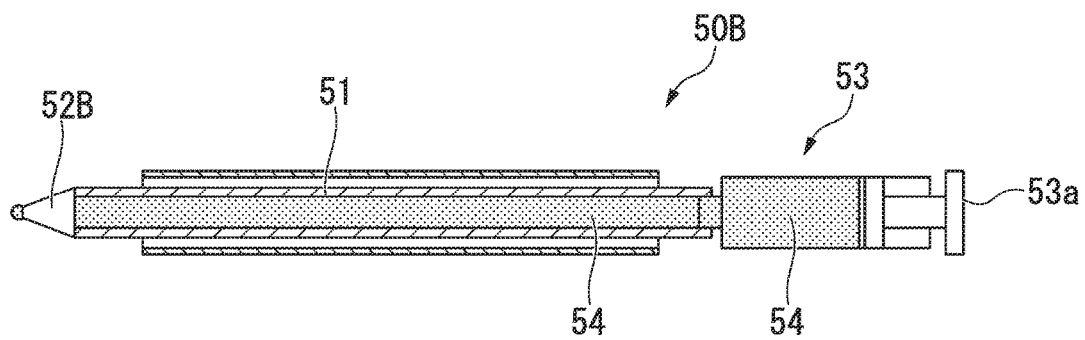
FIG. 7 is a view illustrating an example of a recording jig.

Examples of the recording jig are illustrated in FIGS. 6 and 7. A recording jig 50A illustrated in FIG. 6 and a recording jig 50B illustrated in FIG. 7 has the same basic configuration. That is, the recording jigs includes an elongated insertion part 51 having flexibility, a drawing part provided at a tip part of the insertion part 51, and a printing material supply part provided at a base end part of the insertion part 51.

The insertion part 51 is a tubular member having a dimension such that the insertion part is insertable into the channel of the endoscope, and an internal space thereof is filled with a printing material 54, such as ink. The insertion part 51 is inserted through a sheath 55. In the examples of the recording jigs 50A and 50B, the printing material supply part is a syringe 53, and can supply the printing material 54 into the insertion part 51 by operating a piston 53a.

The configuration of the drawing part is not particularly limited as long as the drawing part can perform printing using the printing material 54 to be supplied from the insertion part 51, and structures or the like of well-known pens and pencils can be adopted appropriately. A felt-pen-like drawing part 52A is illustrated in FIG. 6, and a ball-point-like drawing part 52B is illustrated in FIG. 7.

While the organ model for endoscope of the invention has been described above using the one embodiment, the technical scope of the invention is not limited to the above embodiment. Combinations of constituent elements can be changed, various alternations can be added to the respective constituent elements, or omissions can be made, without departing from the concept of the invention.

For example, in the invention, the basic shape part formed in imitation of the shape of an internal organ is not necessarily flexible. However, if the basic shape part is more flexible, training or the like can be performed with a sensation more similar to an actual internal organ, which is preferable.

Additionally, by splitting the basic shape part into three or more and by attaching the connecting members to respective connection sites, thereby allowing the tissue holding part to be attached to two or more positions of the basic shape part, diversities, such as training, can be further improved. In this case, if the connecting members that face each other are configured so as to be capable of being coupled together without sandwiching the tissue holding part therebetween, a change in the position where the tissue holding part is attached becomes easy, which is more preferable.

Figure 8:
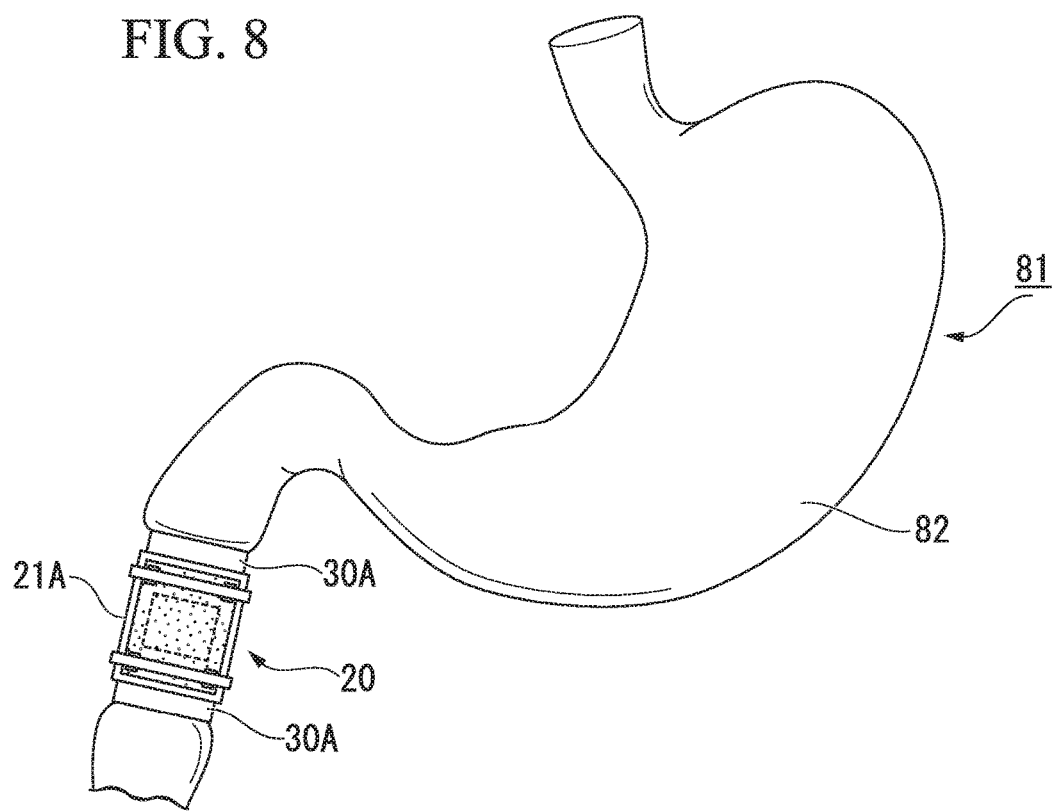
FIG. 8 is a view illustrating a modification example of the organ model for endoscope related to the invention.

Moreover, a target internal organ is not limited to the large intestine, either. In an organ model 81 for endoscope of a modification example illustrated in FIG. 8, the tissue holding part 20 is attached to a position equivalent to a pyloric region of the basic shape part 82 that imitates the shape of the stomach. In the organ model 81 for endoscope, the tissue holding part 20 may be configured so as to be attached to a cardiac region.

In addition, an example in which the main body of the tissue holding part enters the connecting members of the basic shape part, and both are connected together has been described in the above-described embodiment. However, instead of this, a configuration in which the internal diameter of a main body 21A is made greater than the external diameter of a connecting member 30A, and the connecting member 30A enters the main body 21A and both are connected together may be adopted as in the organ model 81 for endoscope illustrated in FIG. 8.

What is claimed is:

1. An organ model for endoscope comprising:
   a basic shape part formed by imitating a shape of a tubular organ; and
   a tissue holding part configured to hold a tissue piece and is detachably provided with respect to the basic shape part,
   wherein the tissue holding part includes:
      a main body that is formed in a tubular shape and has a window part communicating with an internal space of the main body, the window being arranged on an outer peripheral surface of the main body; and
      a fixing member that is attached to the main body and is configured to fix the tissue piece on the main body such that at least a portion of the tissue piece overlaps the window part and a peripheral portion of the tissue piece overlapping the window part is fixed to a periphery of the window part; and
   wherein the main body is configured to be rotatable in a circumferential direction of the main body with respect to the basic shape part, in a state where the main body is attached to the basic shape part.

2. The organ model for endoscope according to claim 1, wherein
   the fixing member has a projection part, and
   the main body has a fixing hole that communicates with the internal space of the main body, so that the projection part can enter into the fixing hole.

3. The organ model for endoscope according to claim 2, wherein the fixing hole is provided at a position that does not overlap the window part in an axial direction of the main body.

* * * * *